US005538660A

United States Patent [19]

Macaudiere

[11] Patent Number: 5,538,660
[45] Date of Patent: Jul. 23, 1996

[54] NONAZEOTROPIC MIXTURES CONTAINING DIFLUOROMETHANE AND 1,1,1,2-TETRAFLUOROETHANE, AND THEIR APPLICATIONS AS REFRIGERANT FLUIDS IN AIR CONDITIONING

[75] Inventor: Sylvie Macaudiere, Asnieres, France

[73] Assignee: Elf Atochem S.A., Puteaux, France

[21] Appl. No.: 267,698

[22] Filed: Jun. 29, 1994

[30] Foreign Application Priority Data

Jun. 30, 1993 [FR] France ................................ 93 07975

[51] Int. Cl.$^6$ ........................................................ C09K 5/04
[52] U.S. Cl. ............................... 252/67; 62/114; 252/364; 264/53; 264/DIG. 5; 510/412; 510/433
[58] Field of Search ............................ 252/67, 162, 172, 252/DIG. 9, 364; 62/114; 264/53, DIG. 5

[56] References Cited

U.S. PATENT DOCUMENTS 4,810,403  3/1989  Bivens et al. ................................ 252/67

FOREIGN PATENT DOCUMENTS

| 705327 | 3/1965 | Canada . |
|---|---|---|
| 430169 | 6/1991 | European Pat. Off. . |
| 0430171 | 6/1991 | European Pat. Off. . |
| 0509673 | 10/1992 | European Pat. Off. . |
| 5-17753 | 1/1993 | Japan . |
| 5-85967 | 4/1993 | Japan . |
| 6-65561 | 3/1994 | Japan . |
| 6-212148 | 8/1994 | Japan . |
| 92/11338 | 7/1992 | WIPO . |
| 92/16597 | 10/1992 | WIPO . |
| 92/16596 | 10/1992 | WIPO . |

OTHER PUBLICATIONS

Handbook of Chemistry and Physics, 63rd Edition, Boiling Point of Tetrafluoromethane, C–373, 1983.

*Primary Examiner*—Christine Skane
*Attorney, Agent, or Firm*—Spencer & Frank

[57] ABSTRACT

In order to replace the chlorodifluoromethane in air conditioning systems, the invention proposes the use, as refrigerant fluid, of a mixture containing by mass from 26 to 34% of difluoromethane, from 56 to 73% of 1,1,1,2-tetrafluoroethane and from 1 to 10% of tetrafluoromethane or octafluoropropane.

3 Claims, No Drawings

NONAZEOTROPIC MIXTURES CONTAINING DIFLUOROMETHANE AND 1,1,1,2-TETRAFLUOROETHANE, AND THEIR APPLICATIONS AS REFRIGERANT FLUIDS IN AIR CONDITIONING

FIELD OF THE INVENTION

The present invention relates to the field of refrigeration, and more particularly to nonazeotropic mixtures of refrigerant fluids which have little or no action on the environment, for the replacement of chlorofluoro carbons (CFCs) or chlorofluorohydrocarbons (HCFCs) in air conditioning systems.

BACKGROUND OF THE INVENTION

These systems used in air conditioning are operated in accordance with a thermodynamic cycle which is defined in general by an evaporation temperature of between 0° and 10° C. (most often 7° C.), a condensation temperature of between + and 55° C., a liquid subcooling of the order of −5° C. and a vapor superheat of at least 10° C.

The refrigerant fluid currently used in air conditioning is chlorodifluoromethane (called HCFC 22). However, it is now established that, because of their coefficient of reaction with ozone, HCFCs—and in particular HCFC 22—will sooner or later have to be replaced by refrigerant fluids which no longer contain chlorine and which, for this reason, are less aggressive with regard to the environment.

In order to replace HCFC 22 in existing air conditioning installations, the substitute must have thermodynamic properties—in particular a coefficient of performance (COP) and a refrigerating capacity— which are as close as possible to those of HCFC 22.

Moreover, for the good stability of the product and the durability of the material, it is desirable that the discharge temperature does not exceed that of HCFC 22 by more than about 5° C. Finally, the substitute must be nonflammable and remain so should the vapor phase leak.

In comparison with chlorinated compounds, difluoromethane (HFC 32), tetrafluoromethane (FC 14), octafluoropropane (FC 218) and 1,1,1,2-tetrafluoroethane (HFC 134a) show no reaction with ozone and have very little action on the environment.

HFC 32 has the major disadvantage of being flammable. Moreover, the fact that its boiling point is considerably lower than that of HCFC 22 means that it is not suitable for the direct replacement of HCFC 22. Those skilled in the art are aware that a low boiling point involves very high pressures, which render the use of such a fluid impossible in existing systems, for reasons of safety.

HFC 134a, a nonflammable compound, is a good refrigerant fluid in terms of efficiency, but its deficient refrigerating capacity renders its use as a substitute for HCFC 22 impossible.

Mixtures of the two abovementioned HFCs in certain proportions give a good compromise between efficiency and refrigerating capacity but, in these proportions, the mixtures have a vapor phase which is flammable.

DESCRIPTION OF THE INVENTION

It has now been found that mixtures containing by mass from approximately 26 to 34% of HFC 32, from approximately 56 to 73% of HFC 134a and from approximately 1 to 10% of perfluorinated hydrocarbon FC 14 or FC 218 possess, in comparison with the individual compounds, thermodynamic properties which are very close to those of HCFC 22. Moreover, the mixtures according to the invention possess a zero coefficient of reaction with ozone and a greenhouse effect which is lower than that of HCFC 22. Finally, unlike HFC 32 and certain mixtures of HFCs 32/134a, the mixtures according to the invention are nonflammable at 25° C. and remain so should the vapor phase leak.

The mixtures according to the invention can thus be used in air conditioning systems, in particular for the replacement of HCFC 22.

Among the mixtures according to the invention, a very particularly preferred mixture contains about 32% of HFC 32, 65% of HFC 134a and 3% of FC 218.

EXAMPLES

The following examples illustrate the invention without limiting it.

Example 1

This example shows the changes in the pressure and composition of a mixture of HFC 32/HFC 134a/FC 218 during a leak of the vapor phase.

The temperature was maintained constant at 24° C. The pressures were measured using a Heise manometer with a precision greater than ±1%. The vessel is initially charged with approximately 342 g of a mixture containing by mass 33% of HFC 32, 64% of HFC 134a and 3% of FC 218.

The leak of vapor phase is continued until 70% of the initial charge has dissipated. During the experiment, samples of the gas phase are collected and analyzed by the standard means of gas chromatography. The vapor tension is also measured at the same time. The results obtained are collated in the following table.

TABLE 1

| Degree of leakage | Absolute pressure | Composition % by mass | | |
|---|---|---|---|---|
| % | bar | HFC 32 | HFC 134a | FC 218 |
| 0 | 12.04 | 46.2 | 43.4 | 10.4 |
| 7.4 | 11.76 | 47.6 | 42.6 | 9.8 |
| 18.8 | 11.42 | 45.3 | 47 | 7.7 |
| 37.9 | 10.93 | 45.2 | 48.7 | 6.1 |
| 49.3 | 10.39 | 39.3 | 57.1 | 3.6 |
| 60.8 | 9.83 | 34.2 | 63.7 | 2.1 |
| 70.3 | 9.26 | 28.1 | 70.8 | 1.1 |

These data indicate that, with a loss of almost 50% of the initial charge, the vapor tension has changed by less than 14%. Such change means that the mixture cannot be considered as pseudo-azeotropic. However, these data also show that, for a leak of less than 40%, even if the pressure decreases (−9%), the concentrations of vapor phase during the leak remain particularly stable (changes of less than 5.5%) and vary considerably afterwards.

On the other hand, the maximum permissible values for HFC 32 for the mixtures to remain nonflammable at room temperature in mixtures of 32/134a and 32/218 are 56% by weight and 67% by weight respectively.

The ternary mixtures according to the invention are thus nonflammable, and remain so during a leak of vapor, since the maximum content of HFC 32 is 47.6%.

Example 2

This example shows that the vapor tension of nonazeotropic mixtures of HFC 32/HFC 134a/FC 218 is close to that of HCFC 22, over a wide temperature range.

Table 2 collates the data for a mixture containing by mass 33% of HFC 32, 64% of HFC 134a and 3% of FC 218.

TABLE 2

| Temperature | Absolute pressure (bar) | |
|---|---|---|
| (°C.) | Mixture 32/134a/218 | HCFC 22 |
| −30 | 1.75 | 1.63 |
| −15 | 3.38 | 2.96 |
| 0 | 5.61 | 4.98 |
| 15 | 8.82 | 7.89 |
| 30 | 13.32 | 11.92 |
| 45 | 19.34 | 17.29 |
| 60 | 27.10 | 24.26 |

Example 3

This example illustrates the use of the mixtures according to the invention as refrigerant fluids.

The thermodynamic characteristics of various ternary mixtures according to the invention were compared with those of the components on their own, with those of their binary mixtures and with those of HCFC 22, for a standard thermodynamic cycle which is 20 defined as follows:

| | |
|---|---|
| Condensation temperature: | +43° C. |
| Evaporation temperature: | +7° C. |
| Liquid subcooling: | −5° C. |
| Vapour superheat: | +11° C. |

Table 3 summarizes the thermodynamic characteristics observed under these conditions for HFC 32, FC 218, HFC 134a and mixtures thereof.

TABLE 3

| Composition (%) mass HFC 32/HFC 134a/FC 218 | Shift in temperature °C. | COP* | Refrigerating capacity, volumetric* | difference in discharge temperature* | difference in condensation pressure* bar |
|---|---|---|---|---|---|
| 100/0/0 | 0 | 0.933 | 1.57 | +17 | +10.3 |
| 0/100/0 | 0 | 1.021 | 0.66 | −14 | −5.5 |
| 0/0/100 | 0 | 0.880 | 0.67 | −27 | −2.5 |
| 25/75/0 | 5.8 | 0.979 | 0.89 | −5 | −1.3 |
| 30/70/0 | 6.2 | 0.974 | 0.93 | −3 | −0.5 |
| 35/65/0 | 6.5 | 0.969 | 0.98 | −2 | −0.3 |
| 38/0/62 | 0 | 0.802 | 1.42 | −8 | +14.5 |
| 0/25/75 | 0 | 0.897 | 0.80 | −23 | −0.5 |
| 0/70/30 | 9.2 | 0.952 | 0.75 | −17 | −2.8 |
| 30/60/10 | 13.7 | 0.940 | 0.99 | −4 | +1.2 |
| 25/65/10 | 13.1 | 0.946 | 0.94 | −5.5 | +0.2 |
| 30/65/5 | 10.8 | 0.956 | 0.96 | −3.5 | +0.3 |
| 35/60/5 | 11.1 | 0.951 | 1.01 | −2 | +1.2 |
| 32/65/3 | 9.3 | 0.960 | 0.97 | −2.7 | +0.3 |
| 27/67.5/5.5 | 10.9 | 0.957 | 0.93 | −4.5 | −0.1 |
| 25/70/5 | 10.3 | 0.962 | 0.91 | −5 | −0.5 |

*In relation to HCFC 22

In the same thermodynamic cycle as defined above, the ternary mixture consisting of 31% of HFC 32, 68% of HFC 134a and 1% of FC 14 has the following characteristics in relation to HCFC 22):

| | |
|---|---|
| shift in temperature: | 16.8°C. |
| COP*: | 0.943 |
| refrigerating capacity, volumetric*: | 0.96 |
| difference* in discharge temperature: | −1.5°C. |
| difference* in condensation pressure: | 0.45 bar |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. Nonazeotropic mixture comprising by mass from 26 to 34% of difluoromethane, from 56 to 73% of 1,1,1,2-tetrafluoroethane and from 1 to 10% of tetrafluoromethane.

2. Method for cooling comprising using the mixture according to claim 1 as a refrigerant fluid for air conditioning.

3. A nonazeotropic air conditioning refrigerant fluid mixture consisting essentially of by mass from 26% to 34% of difluoromethane, from 56% to 73% of 1,1,1,2-tetrafluoroethane, and 1%–10% of tetrafluoromethane; said mixture being nonflammable at 25° C. and remaining nonflammable in the event of a vapor phase leak.

* * * * *